US009554760B2

(12) United States Patent
Rodrigues et al.

(10) Patent No.: US 9,554,760 B2
(45) Date of Patent: Jan. 31, 2017

(54) METHOD AND APPARATUS FOR REDUCING THE RECOVERY TIME DUE TO POLARIZATION WITHIN AN IMAGING DEVICE

(71) Applicant: TOSHIBA MEDICAL SYSTEMS CORPORATION, Otawara (JP)

(72) Inventors: Miesher Lage Rodrigues, Buffalo Grove, IL (US); Gin Chung Wang, Lincolnshire, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 79 days.

(21) Appl. No.: 14/703,332

(22) Filed: May 4, 2015

(65) Prior Publication Data

US 2016/0324493 A1 Nov. 10, 2016

(51) Int. Cl.
*G01N 23/00* (2006.01)
*A61B 6/00* (2006.01)
*A61B 6/03* (2006.01)
*A61B 6/08* (2006.01)

(52) U.S. Cl.
CPC ............ *A61B 6/4241* (2013.01); *A61B 6/035* (2013.01); *A61B 6/08* (2013.01)

(58) Field of Classification Search
CPC ........ A61B 6/4241; A61B 6/42; A61B 6/4208
USPC ........................ 378/19, 22, 44, 46
See application file for complete search history.

(56) References Cited

U.S. PATENT DOCUMENTS

| | | | |
|---|---|---|---|
| 2008/0164418 A1* | 7/2008 | Shahar ...................... | G01T 1/24 250/370.01 |
| 2013/0041628 A1* | 2/2013 | Han .......................... | G01T 1/17 702/189 |
| 2013/0221241 A1* | 8/2013 | Rowlands ............... | H01L 31/115 250/473.1 |

* cited by examiner

*Primary Examiner* — Jason McCormack
(74) *Attorney, Agent, or Firm* — Oblon, McClelland, Maier & Neustadt, L.L.P.

(57) ABSTRACT

A computed tomography (CT) image apparatus includes a plurality of photon-counting detectors (PCD); and processing circuitry configured to obtain a photon count of a PCD of the plurality of PCDs, compare the obtained photon count to a predetermined photon-count threshold, and apply an external light source to the PCD when the obtained photon count is larger than the predetermined photon-count threshold.

20 Claims, 10 Drawing Sheets

METHOD AND APPARATUS FOR REDUCING THE RECOVERY TIME DUE TO POLARIZATION WITHIN AN IMAGING DEVICE

FIELD

The exemplary embodiments described herein relate to computed tomography (CT) systems that use photon-counting detectors.

BACKGROUND

CT systems and methods are widely used, particularly for medical imaging and diagnosis. CT systems generally create images of one or more sectional slices through a subject's body. A radiation source, such as an X-ray tube, irradiates the body from one side thereof. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

Photon-counting detectors (PCDs) are configured to acquire the spectral nature of the X-ray source, rather than the energy integration nature acquired by conventional CT detectors. To obtain the spectral nature acquired by the conventional CT detector, the photon-counting detectors split the X-ray beam into its component energies or spectrum bins, and count a number of photons in each of the bins. The use of the spectral nature of the X-ray source in CT is often referred to as "spectral CT." Since spectral CT involves the detection of transmitted X-rays at two or more energy levels, spectral CT generally includes dual-energy CT by definition.

Semiconductor-based photon-counting detectors used in spectral CT can detect incident photons and measure photon energy for each event. However, due to the interaction depth and the ballistic deficit, the measured photon energy cannot be related to incident photon energy uniquely. Moreover, a high flux can cause pileup and polarization, which ultimately causes the photon-counting detector to saturate. When charges are trapping inside the material in polarization, the internal electronic field of the material is changed and the recovery time of the PCD is extended. Therefore, currently available photon-counting detectors still require solutions to resolve issues related to polarization, in order to increase the accuracy of measuring the photon energy.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

In one embodiment, there is provided a computed tomography (CT) image apparatus, comprising: a plurality of fixed photon-counting detectors (PCD) provided on a circular ring; and processing circuitry configured to obtain a photon count of a PCD of the plurality of PCDs; compare the obtained photon count to a predetermined photon-count threshold; and apply an external light source to the PCD when the obtained photon count is larger than the predetermined photon-count threshold.

In another embodiment, there is provided a computed tomography (CT) image apparatus, comprising: a plurality of photon-counting detectors (PCD); and processing circuitry configured to obtain a leakage current of a PCD of the plurality of PCDs; compare the obtained leakage current to a predetermined leakage-current threshold; and apply an external light source to the PCD when the obtained leakage current is larger than the predetermined leakage-current threshold.

In another embodiment, there is provided an imaging method for a CT apparatus that includes a plurality of photon-counting detectors (PCDs), the method comprising: obtaining a photon count of a PCD of the plurality of PCDs; comparing the obtained photon count to a predetermined photon-count threshold; and applying an external light source to the PCD when the obtained photon count is larger than the predetermined photon-count threshold.

Figure 1:
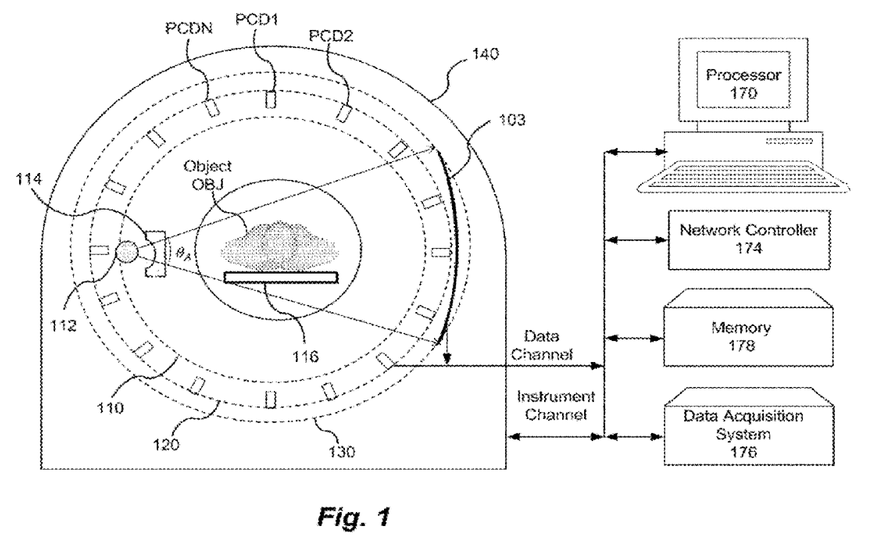
FIGS. 1 and 2 illustrate exemplary CT scanner systems.
Figure 2:
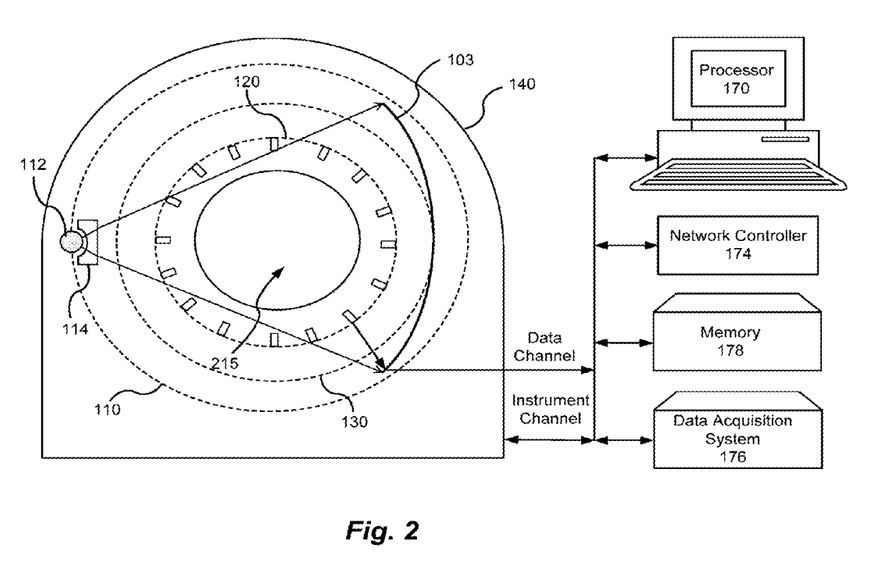

FIG. 1 and FIG. 2 show schematic views of CT scanner systems with hybrid systems having energy-integrating detectors arranged in a third-generation geometry and photon-counting detectors (PCDs) arranged in a fourth-generation geometry. FIG. 1 shows a coupled-ring topology with the X-ray source 112 inside the ring of PCDs and the X-ray detector 103 outside the ring of PCDs. In contrast, FIG. 2 shows an inner-ring topology with both the X-ray source 112 and the X-ray detector 103 outside the ring of PCDs.

Illustrated in FIG. 1 is one implementation for placing the PCDs in a predetermined fourth-generation geometry in combination with a detector 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector 103.

Also shown in FIG. 1 is circuitry and hardware for acquiring, storing, processing, and distributing X-ray projection data. The circuitry and hardware include: a processor 170, a network controller 174, a memory 178, and a data acquisition system 176.

In one implementation, the X-ray source 112 and the collimator/filter 114 are fixedly connected to a rotational component 110 that is rotatbly connected to a gantry 140. The X-ray detector is similarly fixedly connected to a rotational component 130 that is rotatably connected to the gantry 140. The PCDs are fixedly connected to a circular component 120 that is fixedly connected to the gantry 140. The gantry 140 houses many components of the CT scanner.

The gantry of the CT scanner also includes an open aperture 215 (shown in FIG. 2) enabling the object OBJ that is arranged on a table 116 positioned in a projection plane of the X-rays traveling from the X-ray source to the PCDs and detector 103. The "projection plane" is a volume wherein X-rays pass from the X-ray source 112 to the detectors including the PCDs and the detector 103. The "object space" is the intersection of the projection plane and the open aperture 215 of the gantry. The "image space" includes the union of projection planes corresponding to all projection angles of the X-ray source 112 as the X-ray source 112 rotates around the aperture of the gantry. The image space is generally larger than the object space enabling image reconstruction for a volume extending beyond the dimension of the object.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 1 includes a detector 103 having energy-integrating detectors arranged in a conventional third-generation geometry. The detector elements in the detector 103 can be more densely placed along the detector surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 120 in a gantry. In one implementation, the photon-counting detectors PCD1 through PCDN are fixedly placed on the circular component 120 at predetermined equidistant positions. In an alternative implementation, the photon-counting detectors PCD1 through PCDN are fixedly placed on the circular component 120 at predetermined non-equidistant positions. The circular component 120 remains stationary with respect to the object OBJ and does not rotate during the data acquisition.

Both the X-ray source 112, collimator 114 (e.g., a bow-tie filter), and the detector 103 rotate around the object OBJ while the photon-counting detectors PCD1 through PCDN are stationary with respect to the object OBJ. In one implementation, the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector 103 is mounted at a diametrically opposed position from the X-ray source 112 across the object OBJ and rotates outside the stationary circular component 120, on which the photon-counting detectors PCD1 through PCDN are fixed in a predetermined sparse arrangement.

In one implementation, the X-ray source 112 optionally travels a helical path relative to the object OBJ, wherein the table 116 moves the object OBJ linearly in a predetermined direction perpendicular to the rotational plane of the rotational portion 110 as the rotational portion 110 rotates the X-ray source 112 and detector 103 in the rotational plane.

The motion of the rotational portion 110 around the object OBJ is controlled by a motion control system. The motion control system can be integrated with a data acquisition system or can be separate, providing one-way information regarding the angular position of the rotational portion 110 and the linear position of the table 116. The motion control system can include position encoders and feedback to control the position of the rotational portion 110 and the table 116. The motion control system can be an open-loop system, a closed-loop system, or a combination of an open-loop system and a closed-loop system. The motion control system can use linear and rotary encoders to provide feedback related to the position of the rotational portion 110 and the position of the table 116. The motion control system can use actuators to drive the motion of the rotational portion 110 and the motion of the table 116. These positioners and actuators can include: stepper motors, DC motors, worm drives, belt drives, and other actuators known in the art.

The CT scanner also includes a data channel that routes projection measurement results from the photon-counting detectors and the detector 103 to a data acquisition system 176, a processor 170, memory 178, network controller 174. The data acquisition system 176 controls the acquisition, digitization, and routing of projection data from the detectors. The data acquisition system 176 also includes radiography control circuitry to control the rotation of the annular rotational portion 110 and 130. In one implementation, data acquisition system 176 will also control the movement of the table 116, the operation of the X-ray source 112, and the operation of the X-ray detectors. The data acquisition system 176 can be a centralized system or alternatively it can be a distributed system. In one implementation, the data acquisition system 176 is integrated with the processor 170. The processor 170 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 170 and the data acquisition system 176 can make use of the memory 178 to store, e.g., projection data, reconstructed images, calibration data and parameters, and computer programs.

The processor 170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 178 can be a hard disk drive, CD-ROM drive, DVD drive, FLASH drive, RAM, ROM or any other electronic storage known in the art.

The network controller 174, such as an Intel Ethernet PRO network interface card from Intel Corporation of America, can interface between the various parts of the CT scanner. Additionally, the network controller 174 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 112 is a single source emitting a broad spectrum of X-ray energies. In another implementation, the X-ray source 112 is configured to perform a kV-switching function for emitting X-ray radiation at a predetermined high-level energy and at a predetermined low-level energy. In still another embodiment, the X-ray source 112 includes multiple X-ray emitters, each emitter being spatially and spectrally distinct.

The detector 103 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 2 illustrates an inner ring topology for a CT scanner. The primary difference between the CT scanner in FIG. 1 and the CT scanner in FIG. 2 is that, in FIG. 2, the X-ray source 112 and the rotational component 110 to which the X-ray source 112 is fixed are outside the circular component 120 to which the PCDs are fixed. In one implementation, the back surface of each PCD is provided a protective rear cover to shield the PCDs from irradiation from behind as the X-ray source 112 travels outside the circular component 120 of the sparsely placed photon-counting detectors.

Both the X-ray source 112, collimator 114 (e.g., a bow-tie filter), and the detector 103 rotate around the object OBJ in aperture 215 while the photon-counting detectors PCD1 through PCDN are stationary with respect to the object OBJ in aperture 215. In one implementation, the X-ray source 112 and collimator 114 are mounted on the first rotational component 110 mounted in the gantry 140 so that the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector 103 having energy-integrating detectors arranged in a third-generation geometry is mounted on the second rotational component 130 that is rotatably fixed to the gantry 140. The detector 103 is maintained at a position diametrically opposed position from the X-ray source 112 with the object OBJ in the intermediary space between the X-ray source 112 and the detector 103— the rotational components 110 and 130 rotating outside the stationary circular component 120, on which the photon-counting detectors PCD1 through PCDN are fixed in a predetermined sparse arrangement.

Figure 3A:
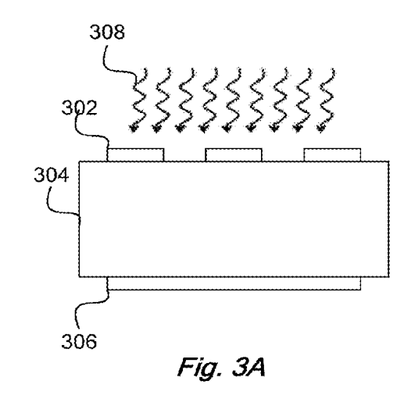
FIG. 3A is a cross-section schematic of a semiconductor detecting device.

FIG. 3A is a schematic cross-section of a semiconductor detecting device, which includes a detector body 304, a cathode surface 306, and an anode surface 302. The detector body 304 is formed of an appropriate planar semiconductor material. When photons 308 are directed at the cathode surface, the photons penetrate the detector body and each photon is absorbed at an absorption depth within the detector body 304. When a photon interacts with the detector body 304 while being absorbed, the detector body 304 generates a plurality of electrons and holes. The electrons and the holes thus generated are collected by the anode 302 and the cathode 306, respectively. The collected charges are measured at the anodes to calculate the energy of the absorbed photon.

Figure 3B:
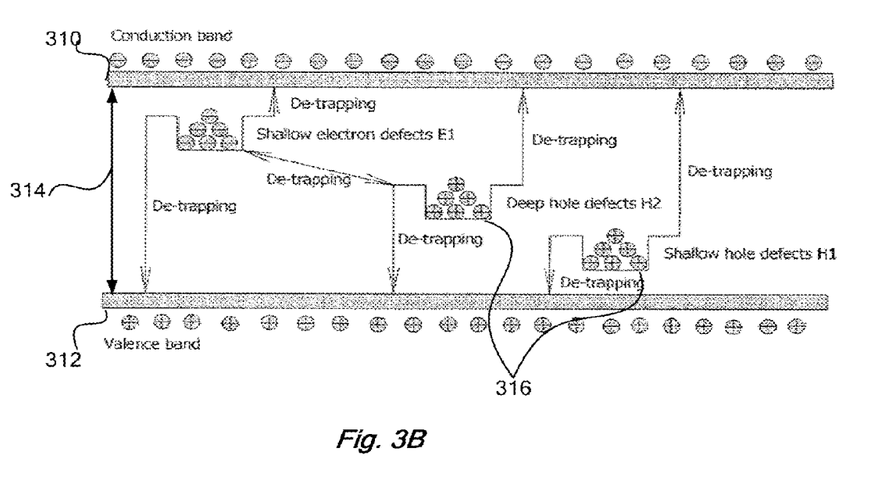
FIG. 3B illustrates exemplary externally stimulated paths for trapped space charges in a detector.

As shown in FIG. 3B, the semiconductor material of the detecting device has a valence band 312 and a conduction band 310, separated by a bandgap 314. Ionizing radiation from the X-ray source absorbed in the detecting device can cause electrons to jump the bandgap 314, forming electron-hole pairs, e.g., electrons in conduction band 310 and corresponding holes in valence band 312. In the detecting device, electrons drift to the anode and the holes drift to the cathode. Holes, due to their poor transport properties, e.g., mobility and mobility-life time product, get easily trapped in shallow and deep defects in the crystal structure of image detecting device's crystal structure. Thus, the energy bandgap can include some hole-trap energy levels 316. The holes are trapped until they recombine with electrons.

A trapped hole, if allowed to remain, can create a polarization effect in the detecting device, e.g., by causing some electrons from the electron-hole pairs generated by X-ray photon absorption to be attracted to the trapped holes, instead of to the anodes. The polarization effect of the trapped-hole may lead to measurement of the X-ray photon energy and of the location of the absorption of the photon to become inaccurate.

Existing solutions to reduce the polarization of detecting devices have limitations. A method of adding a continuous irradiation source to the detecting device to thermally removed the trapped space charges, can stimulate some electron-hole pairs in the field of view (FOV). The FOV is the region exposed to the X-ray source to detect the transmitted X-ray. The detecting devices within the FOV detect not only the electron-holes generated through the X-ray source, but also the electron-holes generated by the continuous irradiation source.

The probability per unit time that an electron-hole pair is thermally generated is defined by equation (1):

$$P(T) = CT^{\frac{3}{2}} \times \exp\left(-\frac{E_g}{2KT}\right) \quad (1)$$

wherein T is the absolute temperature, $E_g$ is the bandgap energy, k is the Boltzmann constant, and C is a proportionality constant characteristic of the material.

Figure 4A:
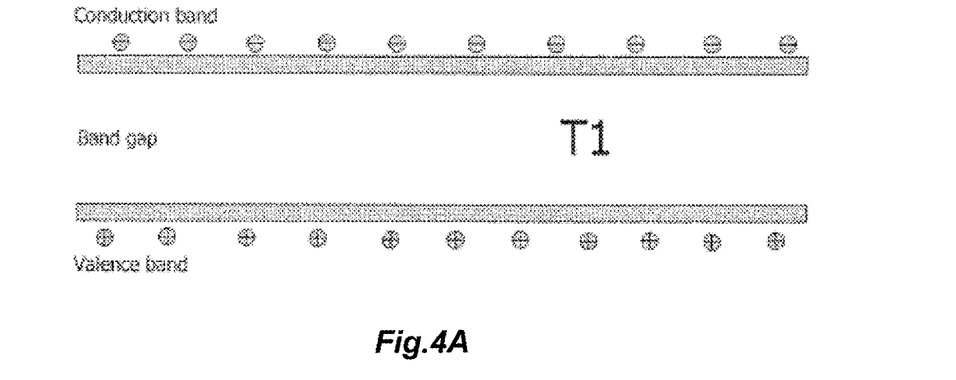
FIGS. 4A and 4B illustrate band gaps of ideal detecting devices at different temperatures.
Figure 4B:
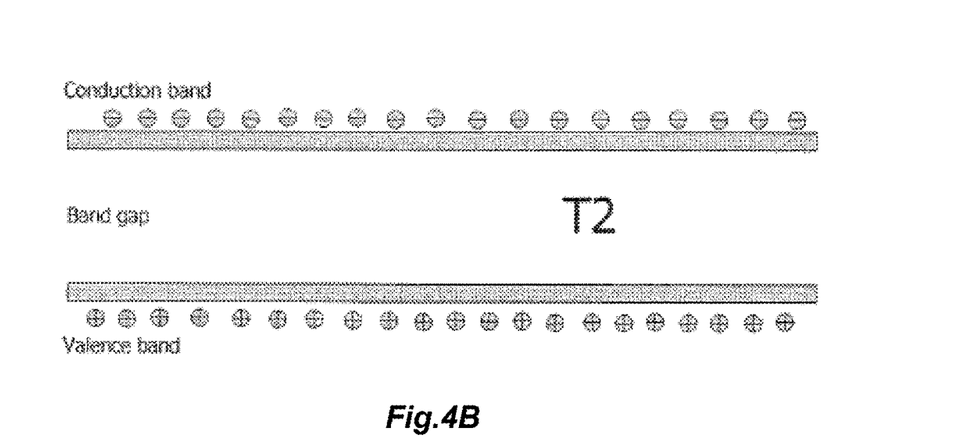

FIGS. 4A and 4B show thermally stimulated charge carriers at the valence and conduction bands of ideal detecting devices at temperatures T1 and T2, where T1<T2.

Equation (1) and FIGS. 4A and 4B show that, at high temperature, a continuous irradiation source generates additional hole-electron pairs and the generation of thermally stimulated electron-hole pairs is a random process that degrades the measured signal-to-noise (SNR).

Figure 5:
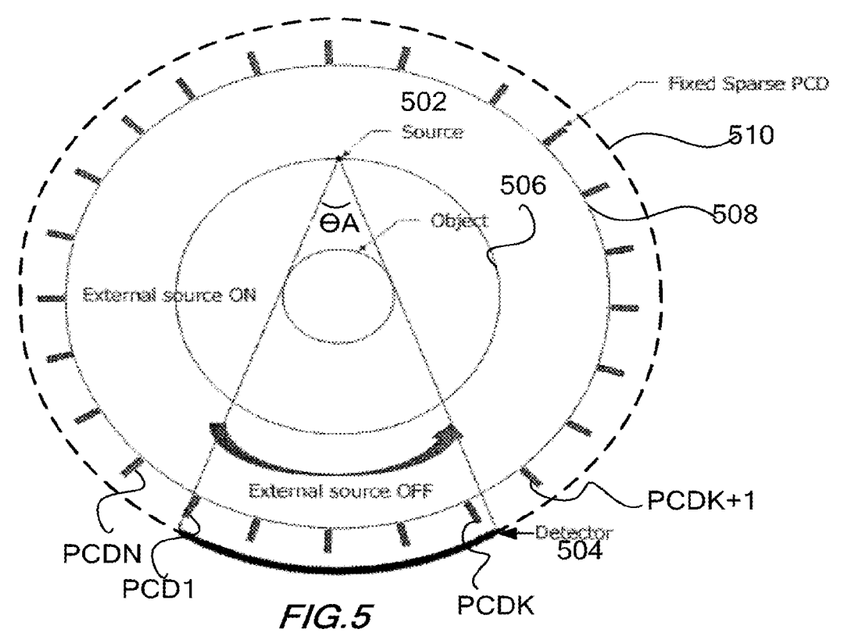
FIG. 5 is a schematic representation of a CT scanner including an external source of excitation in accordance with a present embodiment.

FIG. 5 is a schematic representation of a CT scanner including an external source of excitation in accordance with a disclosed embodiment. The diagram illustrates that PCDs are placed in a predetermined fourth-generation geometry in combination with a detector in a predetermined third-generation geometry in the CT scanner system. The diagram illustrates the relative relationship among an object to be scanned, an X-ray source 502, an X-ray detector 504, and the fixed photon-counting detectors PCD1 through PCDN. A predetermined number of the photon-counting detectors (PCDs) is sparsely placed around the object in a predetermined geometry such as a circle. For example, the photon-counting detectors PCD1 through PCDN are fixedly placed on a predetermined circular component 508 in the gantry. Furthermore, in one embodiment, the photon-counting detectors PCD1 through PCDN are fixedly placed on the circular component 508 at predetermined equidistant positions in one embodiment. In another embodiment, the photon-counting detectors PCD1 through PCDN are fixedly placed on the circular component 508 at predetermined non-equidistant positions. The circular component 508 remains stationary with respect to the object.

Both the X-ray source 502 and the X-ray detector 504 rotate around the object while the photon-counting detectors PCD1 through PCDN are stationary with respect to the object. In one embodiment, the X-ray source 502 is mounted on a first rotating portion 506, so that the X-ray source 502 projects X-rays with a predetermined source fan beam angle θA towards the object while the X-ray source 502 rotates around the object inside the sparsely placed photon-counting detectors PCD1 through PCDN. Furthermore, an additional detector 504 is mounted on a second rotating portion 510 in the third-generation geometry. The rotating portion 508 mounts the detector 504 at a diametrically opposed position from the X-ray source 502 across the object and rotates outside the stationary circular component 508 on which the photon-counting detectors PCD1 through PCDN are fixedly placed in a predetermined sparse manner.

As the X-ray source 502 and the detector 504 rotate around the object, the photon-counting detectors PCDs and the detector 504 respectively detect the transmitted X-ray during data acquisition. The photon-counting detectors PCD1 through PCDN intermittently detect the X-rays that have been transmitted through the object and individually output a number of photons for each of a predetermined number of energy levels. On the other hand, the detector elements in the detector 504 continuously detect the X-rays that have been transmitted through the object and output the detected signals as the detector 504 rotates.

In general, the photon-counting detectors PCD1 through PCDN are sparsely positioned along the circular component 508. Although the photon-counting detectors PCD1 through PCDN acquire sparse view projection data, the acquired projection data is sufficient for at least dual-energy (DE) reconstruction. In addition, the detector 504 also acquires another set of projection data, and the projection data from the detector 504 is used to generally improve image quality.

One embodiment includes using an external source of excitation, e.g., an infrared light source, integrated within or adjacent to each PCD device, providing means to reduce the recovery time of the PCDs after polarization, by promoting de-trapping of trapped space charges. As shown in FIG. 5, when the X-ray source 502 projects X-rays with a predetermined source fan beam angle θA towards the object, PCD1 through PCDK are exposed to the X-ray resource to detect the transmitted X-rays, while PCDK+1 to PCDN are not in the FOV of the X-ray source, and thus are not exposed to the X-rays. Thus, during this time, the external infrared light source integrated with or adjacent to PCD1 through PCDK are turned off, to avoid additional noise added to the detected X-ray signal. On the other hand, the external light sources integrated with or adjacent to PCDK+1 to PCDN are turned on, to reduce the recovery time of those PCDs after polarization.

To best reduce the polarization effects without degrading the signal-to-noise ratio of a PCD, a local control circuit is used, wherein the external source, e.g., an infrared (IR) source, is controlled by the local control circuit. In another embodiment, a single high-level controller can be used to control the IR sources.

Figure 10:
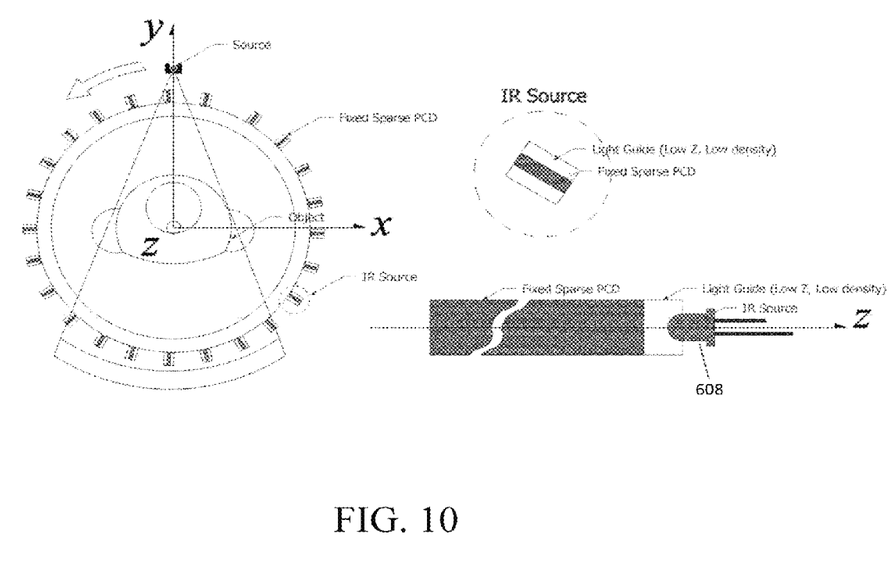
FIG. 10 illustrates IR sources arranged adjacent to each PCD.

FIG. 10 illustrates an example of IR sources integrated with each PCD. As shown in FIG. 10, an IR source 608 is arranged adjacent to each PCD, and a light guide made of a low Z, low-density material is arranged between the IR source and the PCD. Each IR source 608 is connected to and controlled by a control circuit 606, which is positioned outside the FOV of the X-ray source, as described in more detail below. As noted above, in an alternative embodiment, a single high-level controller or a group of controllers can be used to control the IR sources.

Figure 6:
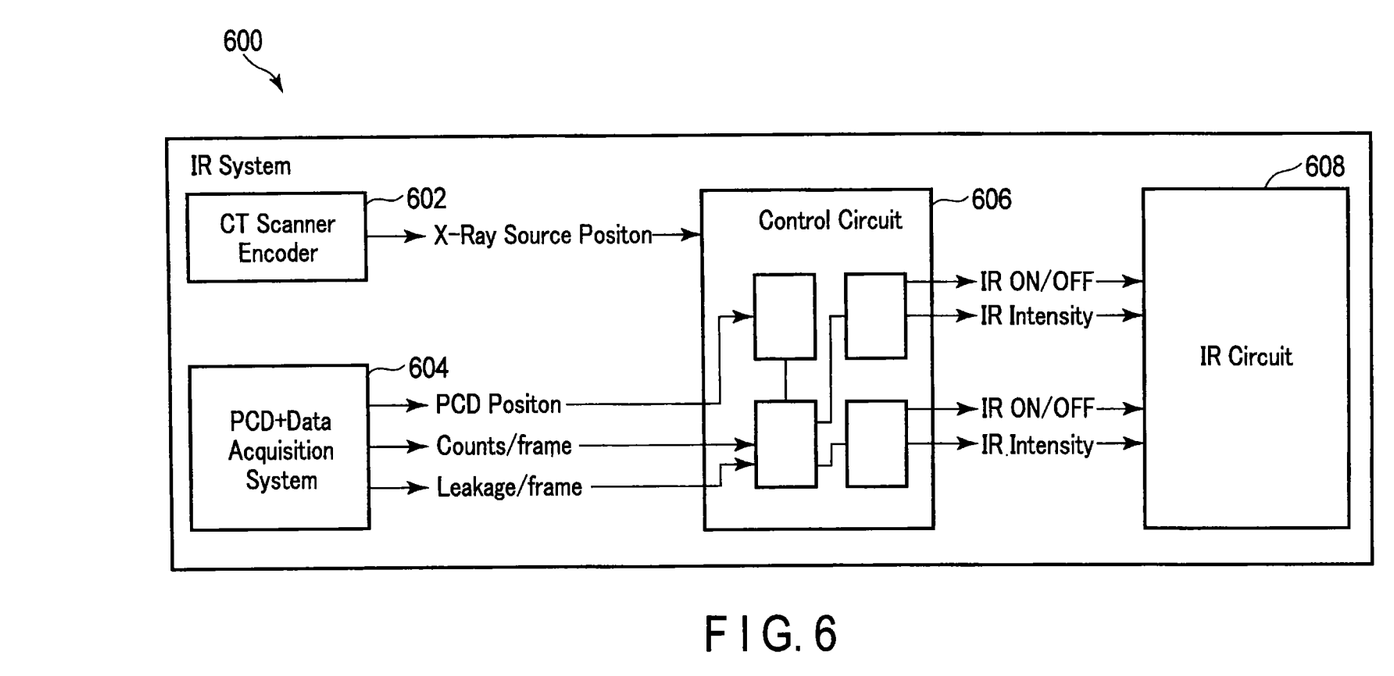
FIG. 6 is an exemplary system diagram of a corrective action infra-red (IR) system.

FIG. 6 is an exemplary system diagram of a corrective-action infrared (IR) system 600. The IR system 600 includes a CT scanner encoder 602, a PCD data acquisition system 604, at least one control circuit 606 and at least one IR source 608. The CT scanner encoder 602 provides X-ray source positions. The PCD data acquisition system 604 acquires information of PCD positions, photon counts, and leakage current at each frame or view. The IR source 608, which deploys IR excitation to the corresponding PCD or PCDs, is controlled by the control circuit 606. The PCDs can be divided into several groups based on their locations. Each PCD, or each group of PCDs, can also have its own control circuit 606. The control circuit 606 turns on/off the corresponding IR source 608 based of the PCD position, the X-ray source position, measured photon counts, measured leakage current, and predetermined threshold levels.

The IR source 608 is controlled in two modes based on the relative position of the corresponding PCD to the X-ray source. The two modes are an "ON-cycle" and an "OFF-cycle."

The ON-cycle is a period of time during which the corresponding PCD or group of PCDs is located within the FOV of the X-ray source. During the ON-cycle, the PCD or the group of PCDs within the FOV might be directly exposed to very high X-ray flux levels due to the absence of attenuation or reduced attenuation in the beam path. The absence of attenuation or reduced attenuation in the beam path can be caused by a reduction of the patient's dimension relative to a bowtie filter. The bowtie filter is an attenuation filer configured to minimize X-ray exposure to edges of the patient where X-ray transmission path lengths are shorter and noise in the projection data has a less degrading impact on overall image quality. The reduction of the patient's dimension can cause un-expected X-ray attenuation because the design of the bowtie filter does not match with a smaller patient.

During the ON-cycle, the control circuit 606 compares the measured counts with a threshold count in each cycle, wherein a cycle is the time that is required for the PCD data acquisition system 604 to acquire photon counts and the leakage current information from the PCD detector. When the photon counts measured at a PCD are above a predetermined threshold level in the ON-cycle, the IR source 608 corresponding to the PCD is turned on with an intensity calculated by the control circuit 606. The turned-on IR circuit stimulates de-trapping of the positive space charges to reduce the effects of polarization. The turned-on IR circuit can be kept at a lower level during the entire ON-cycle instead of being turned off, when the measured photon count is below the predetermined threshold level.

Figure 7:
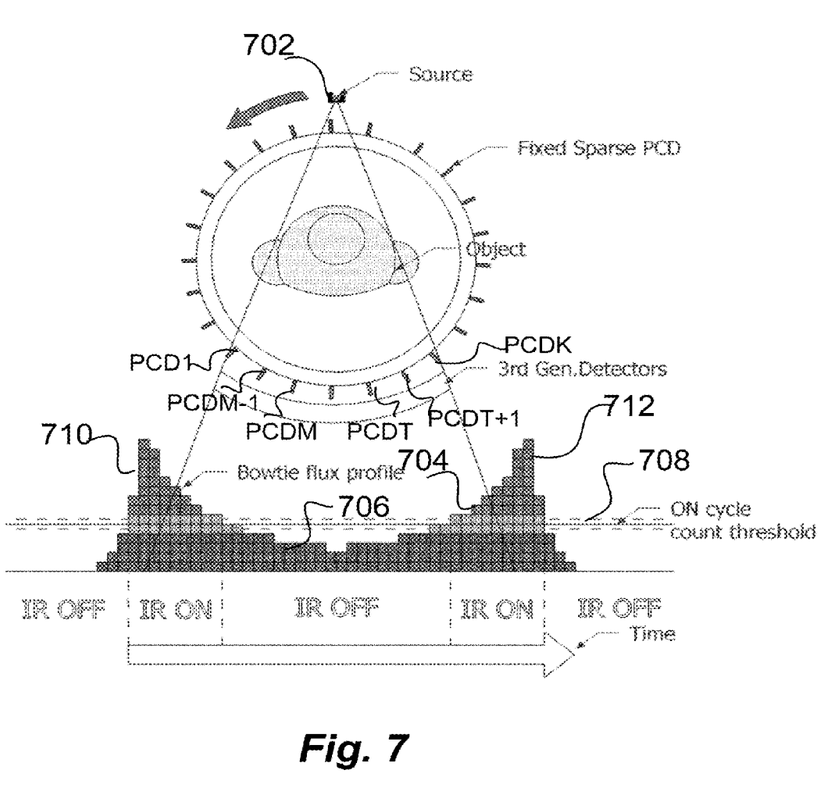
FIG. 7 illustrates an operation process of the IR circuits during the ON-cycle.

FIG. 7 illustrates the operation of the IR sources during the ON-cycle. The photon counts are measured at each PCD as the X-ray source 702 rotates around the CT gantry during the ON-cycle. The measured photon counts are used to generate a bowtie flux profile 704. The bowtie flux profile 704 shows the number of the measured photon counts of each PCD. The photon counts measured at PCDM through PCDT are shown in a sub-region 706 of the bowtie flux profile. In the sub-region 706, the measured photon counts are less than the threshold count 708, and therefore the IR circuits corresponding to PCDM through PCDT are turned off. The photon counts measured at PCD1 through PCDM−1 are shown in a sub-region 710 of the bowtie flux profile, and the photon counts measured at PCDT+1 through PCDK are shown in a sub-region 712 of the bowtie flux profile. In sub-regions 710 and 712, the measured photon counts are larger than the threshold count 708, and therefore the IR circuits corresponding to PCD1 through PCDM−1 and PCDT+1 through PCDK are turned on. Instead of being turned off, the IR control circuits (sources) can stay ON at a lower intensity level.

The OFF-cycle is a period of time when a corresponding PCD or group of PCDs is located out of the FOV of the X-ray source. During the OFF-cycle, the leakage current on the PCD can be high due to space-charge build up, which is generated by the positive charges trapped in deep levels accumulated during the ON-cycle.

During the OFF-cycle, the control circuit 606 compares the measured leakage current with a predetermined threshold current in each cycle. If the measured leakage current is above the predetermined threshold current, the IR source 608 is turned on with an intensity that is calculated by the control circuit 606. The calculated intensity of the IR source will be higher for larger differences between the measured leakage current and the threshold level. For example, the calculated intensity of the IR source will be proportional to the difference between the measured leakage current and the threshold level. The IR circuit can be kept on at lower levels during the entire OFF-cycle instead of being turned off, if the measured leakage current is below the threshold level.

Keeping the IR circuits turned ON at lower levels improves hole-effective drift velocity by reducing the de-trapping time, thus allowing holes to be collected, which is the main cause of space-charge polarization. The drift velocity of holes is much slower than that of electrons (100×), thus there is no significant change in signal induction.

Figure 8:
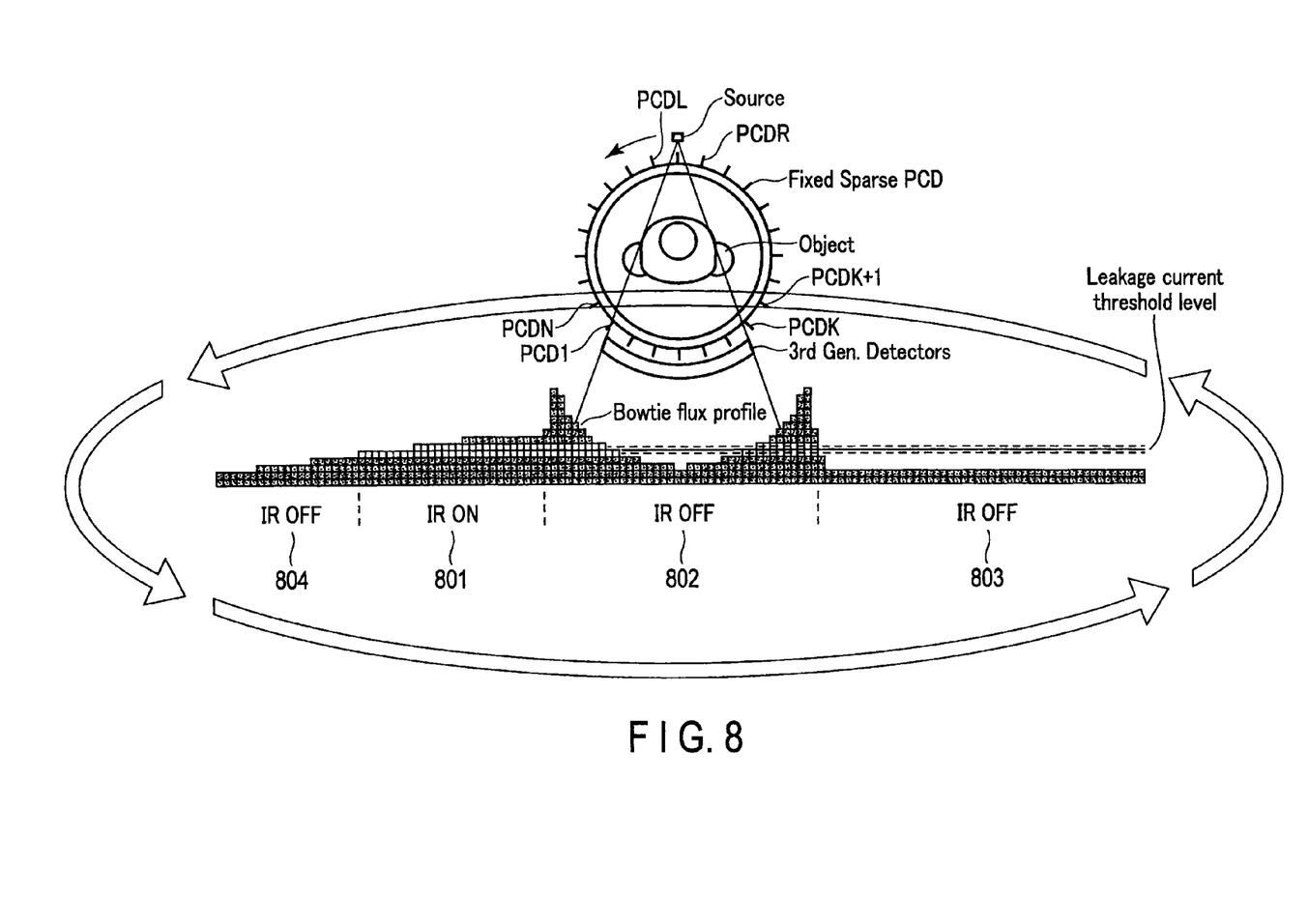
FIG. 8 illustrates an operation process of the IR circuits during the OFF-cycle.

FIG. 8 illustrates the operation of the IR source during the OFF-cycle. The leakage current is measured at each PCD by each data acquisition system 604 as the X-ray source rotates around the CT gantry during the OFF-cycle. The measured leakage currents are compared with a threshold current. The IR sources associated with the PCDs that are located within the FOV are turned off (corresponding to sub-region 802), and the IR sources associated with the PCDs that are located outside of the FOV can be turned on.

The leakage currents measured at PCDs outside the FOV that exceed the threshold are shown in a sub-region 801. In the sub-region 801, the measured leakage currents are above the threshold current, and therefore the IR sources corresponding to, e.g., PCDL through PCDN are turned on. The leakage currents measured at PCDK+1 through PCDR, e.g., are shown in a sub-regions 803 and 804. In sub-regions 803 and 804, the measured leakage currents are smaller than the threshold current, and therefore the IR sources corresponding to PCDK+1 through PCDR are turned off. Instead of being turned completely off, the IR circuits can stay ON at a lower intensity level.

The intensity of an IR source can be regulated, for instance, by the difference between the threshold and the measured value, but can be constant or varied according to the changing rate of the measured quantities, either the photon count or the leakage current.

Figure 9:
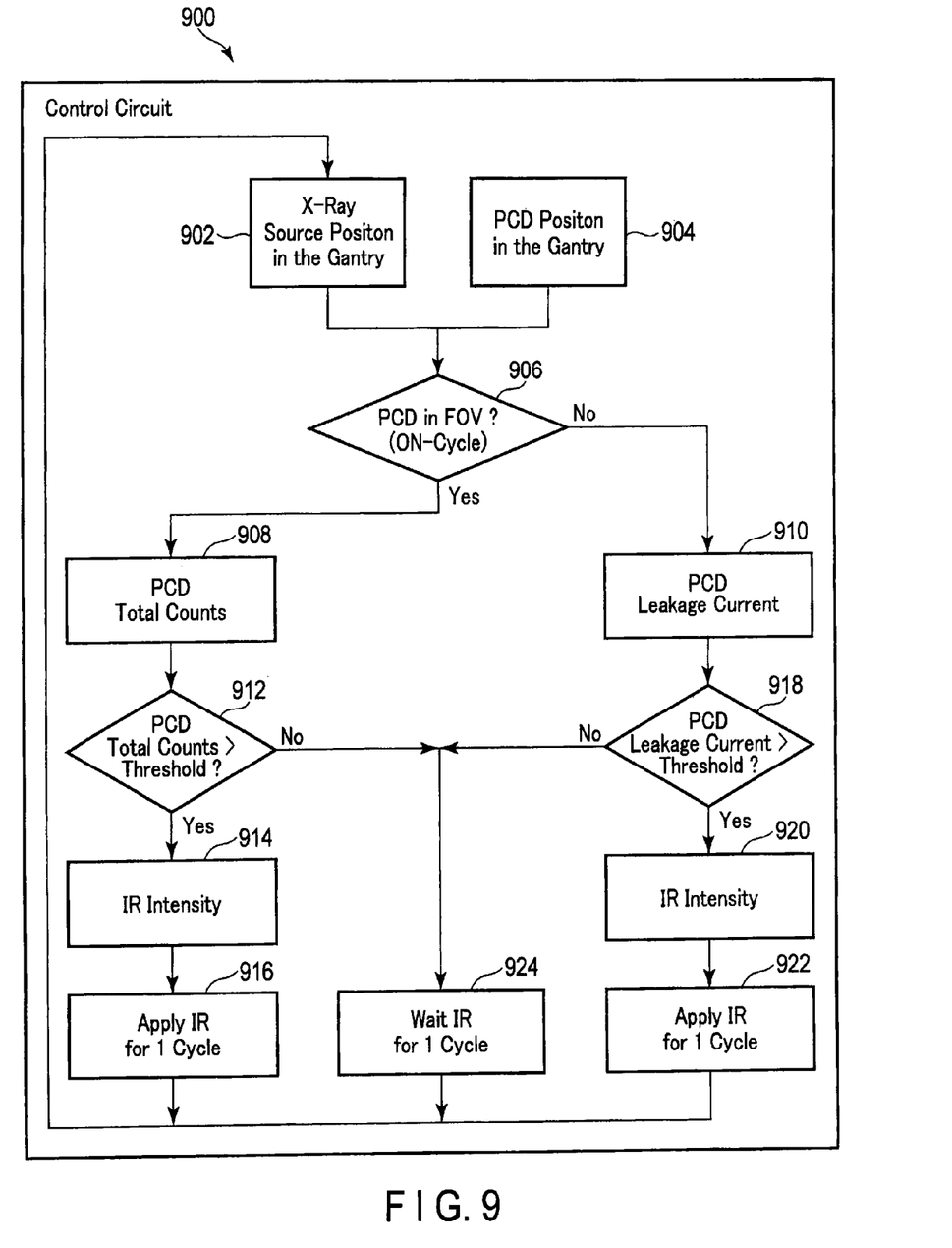
FIG. 9 illustrates an operation of the corrective action system, by way of a flowchart.

Referring to FIG. 9, a flowchart 900 describes an operation of a control circuit.

At step 902, the processing circuitry of the control circuit 606 obtains positions of the X-ray source 502 in the gantry from the CT scanner encoder 602.

At step 904, the processing circuitry of the control circuit 606 obtains positions of the PCD in the gantry from the CT scanner encoder 602.

At step 906, the processing circuitry of the control circuit 606 determines whether the PCD is located in the FOV of the X-ray source. If the PCD is determined to be located within the FOV of the X-ray source 502, the processing circuitry executes step 908. If the PCD is determined to be located outside the FOV of the X-ray source, the processing circuitry executes step 910.

At step 908, the processing circuitry of the control circuit 606 obtains the photon counts of each PCD located within the FOV of the X-ray source 502 during the current cycle from the PCD data acquisition system 604.

At step 912, the processing circuitry of the control circuit 606 determines whether the measured photon counts are larger than a threshold count. If the measured photon counts are larger than the threshold count, the processing circuitry executes step 914. If the measured photon counts are smaller than the threshold count, the processing circuitry executes step 924.

At step 914, the processing circuitry of the control circuit 606 determines the appropriate intensity for the IR sources 608 corresponding to the PCDs with measured photon counts larger than the threshold count.

At step 916, the processing circuitry of the control circuit 606 turns on the IR sources 608 during the current cycle. The intensity of the IR sources 608 can be increased as the difference between the number of the measured photon counts and the threshold number increases.

At step 910, the processing circuitry of the control circuit 606 obtains the leakage currents of each PCD located outside of the FOV of the X-ray source 502 at the current cycle from the PCD data acquisition system 604.

At step 918, the processing circuitry of the control circuit 606 determines whether the measured leakage current is larger than a threshold current. If the measured leakage currents are larger than the threshold current, the processing circuitry executes step 922. If the measured leakage current is smaller than the threshold current, the processing circuitry executes step 924.

At step 920, the processing circuitry of the control circuit 606 determines the appropriate intensity for the IR source 608 corresponding to the PCDs with measured leakage current larger than the threshold count.

At step 922, the processing circuitry of the control circuit 606 turns on the appropriate IR sources 608 during the current cycle. The intensity of the IR source can be increased as the difference between the leakage current and the threshold current increases.

At step 924, the control circuit 606 keeps the IR sources 608 corresponding to the PCDs with measured photon counts or leakage currents smaller than the threshold value off and waits for the next cycle to restart from step 902. Instead of turning off the IR sources 608, the intensity of the corresponding IR sources 608 can be set to a low steady level during the waiting period.

Other external sources, e.g., visible LED, ultraviolet (UV) light sources, and others can be used in combination with or instead of IR sources 608. While PCDs with different band gap energies, e.g., TlBr, CdZnTe, and HgI2 have different responses to external sources, the control circuit disclosed here is designed to provide the same results.

Moreover, intensities and positions of each external source (e.g., each IR source 608) relative to the detecting devices may be optimized to preferentially stimulate de-trapping of positive space charges while sustaining the SNR of the data. The external source integrated with the PCD can be one external source positioned on one side of each PCD operated at a fixed intensity or variable source intensities as a function of time; two external sources positioned one on each side of each imaging detecting device operated at a fixed intensity or variable source intensities as a function of time; multiple external sources positioned at different locations of each imaging detecting device operated at a fixed intensity or variable source intensities as a function of time; or any other combination using the same and/or different external sources.

Furthermore, the control circuit can selectively control the intensity of the external sources, rather than simply turning them ON and OFF.

The present embodiments are suitable for combined third- and fourth-generation CT systems since they take advantage of the time that the PCDs used in the fourth-generation ring, e.g., CdZnTe semiconductor detectors, are not in the direct field of view of the X-ray source, to recover the PCDs from space-charge polarization in a previous cycle. The disclosed embodiments can rapidly recover the PCDs from space-charge polarization to their original operating condition, ready for the next irradiation cycle after being exposed to the external source.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) apparatus, comprising:
a plurality of photon-counting detectors (PCD); and
processing circuitry configured to
obtain a photon count of a PCD of the plurality of PCDs;
compare the obtained photon count to a predetermined photon-count threshold; and
apply an external light source to the PCD when the obtained photon count is larger than the predetermined photon-count threshold.

2. The apparatus of claim 1, further comprising:
a radiation source configured to emit X-rays and to rotate around an object to be scanned; and
a CT detector configured to rotate with the radiation source to detect the emitted X-rays.

3. The apparatus of claim 2, wherein the processing circuitry is further configured to obtain photon counts from only the PCDs that are located within a field-of-view of the radiation source.

4. The apparatus of claim 1, wherein the processing circuitry is further configured to determine an intensity of the external light source, wherein the intensity is determined according to a difference between the obtained photon count and the predetermined photon-count threshold.

5. The apparatus of claim 2, wherein the external light source is one of a visible light source, an ultraviolet light source, and an infrared source.

6. A computed tomography (CT) apparatus, comprising:
a plurality of photon-counting detectors (PCD); and
processing circuitry configured to
obtain a leakage current of a PCD of the plurality of PCDs;
compare the obtained leakage current to a predetermined leakage-current threshold; and apply an external light source to the PCD when the obtained leakage current is larger than the predetermined leakage-current threshold.

7. The apparatus of claim 6, further comprising:
a radiation source configured to emit X-rays and to rotate around an object to be scanned; and
a CT detector configured to rotate with the radiation source to detect the emitted X-rays.

8. The apparatus of claim 7, wherein the processing circuitry is further configured to obtain the leakage current from only the PCDs that are located outside of the field-of-view of the radiation source.

9. The apparatus of claim 6, wherein the processing circuitry is further configured to determine an intensity of the external light source, wherein the intensity is determined according to a difference between the obtained leakage current and the predetermined leakage-current threshold.

10. The apparatus of claim 7, wherein the external light source is one of a visible light source, an ultraviolet light source, and an infrared source.

11. An imaging method for a CT apparatus that includes a plurality of photon-counting detectors (PCDs), the method comprising:
obtaining a photon count of a PCD of the plurality of PCDs;
comparing the obtained photon count to a predetermined photon-count threshold; and
applying an external light source to the PCD when the obtained photon count is larger than the predetermined photon-count threshold.

12. The method of claim 11, further comprising:
obtaining a leakage current of a second PCD of the plurality of PCDs;
comparing the obtained leakage current to a predetermined leakage-current threshold; and
applying a second external light source to the second PCD when the obtained leakage current is larger than the predetermined leakage-current threshold.

13. The method of claim 11, further comprising obtaining photon counts from only the PCDs that are located within a field-of-view of the radiation source.

14. The method of claim 11, further comprising determining an intensity of the external light source, wherein the intensity is proportional to a difference between the obtained photon count and the predetermined photon-count threshold.

15. The method of claim 12, further comprising obtaining the leakage current from only the PCDs that are located outside of the field-of-view of the radiation source.

16. The method of claim 15, further comprising determining the intensity of the second external light source, wherein the intensity is proportional to a difference between the obtained leakage current and the predetermined leakage-current threshold.

17. The method of claim 11, wherein the external light source includes one of a visible light source, an ultraviolet light source, and an infrared source.

18. The apparatus of claim 1, further comprising:
the external light source, wherein the external light source is located on a first side of the PCD and operates at a fixed intensity or variable source intensity as a function of time.

19. The apparatus of claim 18, further comprising an additional external light source located on a second side of the PCD, the second side being different than the first side, the additional light source operating at a fixed intensity or variable source intensity as a function of time.

20. The apparatus of claim 2, wherein the processing circuitry is further configured to apply the external light source to the PCD when the PCD is within a field-of-view of the radiation source and the obtained photon count is larger than the predetermined photon-count threshold.

* * * * *